(12) United States Patent
Hwang et al.

(10) Patent No.: US 11,338,174 B2
(45) Date of Patent: May 24, 2022

(54) METHOD AND SYSTEM OF PLANNING FITNESS COURSE PARAMETERS

(71) Applicant: J-MEX, Hsinchu (TW)

(72) Inventors: Deng-Huei Hwang, Hsinchu (TW); Bing-Ho Tsai, Hsinchu (TW); Meng-Yu Lee, Hsinchu (TW)

(73) Assignee: J-Mex Inc., Hsinchu (TW)

( * ) Notice: Subject to any disclaimer, the term of this patent is extended or adjusted under 35 U.S.C. 154(b) by 528 days.

(21) Appl. No.: 16/234,204

(22) Filed: Dec. 27, 2018

(65) Prior Publication Data

US 2019/0192912 A1    Jun. 27, 2019

(30) Foreign Application Priority Data

Dec. 27, 2017  (TW) ................................ 106146085

(51) Int. Cl.
| | |
|---|---|
| *A63B 24/00* | (2006.01) |
| *A61B 5/11* | (2006.01) |
| *A61B 5/0205* | (2006.01) |
| *A61B 5/00* | (2006.01) |
| *G09B 5/02* | (2006.01) |

(Continued)

(52) U.S. Cl.
CPC ........ *A63B 24/0075* (2013.01); *A61B 5/0024* (2013.01); *A61B 5/01* (2013.01); *A61B 5/02055* (2013.01); *A61B 5/11* (2013.01); *A61B 5/1118* (2013.01); *A61B 5/486* (2013.01); *A61B 5/4866* (2013.01); *A61B 5/681* (2013.01); *A63B 24/0006* (2013.01); *A63B 24/0062* (2013.01); *G09B 5/02* (2013.01); *G09B 19/0038* (2013.01); *G16H 20/30* (2018.01); *A61B 5/02438* (2013.01); *A61B 2503/10* (2013.01); *A61B 2562/0219* (2013.01); *A63B 2024/0015* (2013.01); *A63B 2024/0065* (2013.01); *A63B 2024/0068* (2013.01);

(Continued)

(58) Field of Classification Search
CPC .................................................. A63B 24/0075
USPC ......................................................... 600/301
See application file for complete search history.

(56) References Cited

U.S. PATENT DOCUMENTS

| | | |
|---|---|---|
| 7,905,818 B1 | 3/2011 | Habig |
| 2003/0144829 A1 | 7/2003 | Geatz et al. |

FOREIGN PATENT DOCUMENTS

| | | |
|---|---|---|
| TW | 201716116 A | 5/2017 |
| WO | 2014153201 A1 | 9/2014 |

OTHER PUBLICATIONS

The Office Action for Taiwanese application No. TW201716116 dated Jan. 7, 2019.

*Primary Examiner* — Kesha Frisby

(74) *Attorney, Agent, or Firm* — Haverstock & Owens, a Law Corporation

(57) ABSTRACT

A method for planning parameters of a fitness course is disclosed. The method includes the following steps: generating a plurality of limb motion signals by sensing a plurality of limb motions of a body builder through a sensing module, and sensing a physiological state of the body builder to generate a physiological state signal via the sensing module; obtaining a workout characteristic index (WCI) by performing a first calculation related to the plurality of limb motion signals, and obtaining a physiological effect index (PEI) by performing a second calculation associated with the physiological state signal; obtaining a workout effect index (WEI) by performing a third calculation associated with the WCI and the PEI; and evaluating a plurality of categorical factors (Continued)

associated with the WEI to plan the parameters of the fitness course.

20 Claims, 8 Drawing Sheets

(51) Int. Cl.
*A61B 5/01* (2006.01)
*G16H 20/30* (2018.01)
*G09B 19/00* (2006.01)
*A61B 5/024* (2006.01)

(52) U.S. Cl.
CPC . *A63B 2024/0078* (2013.01); *A63B 2220/803* (2013.01); *A63B 2230/06* (2013.01); *A63B 2230/50* (2013.01)

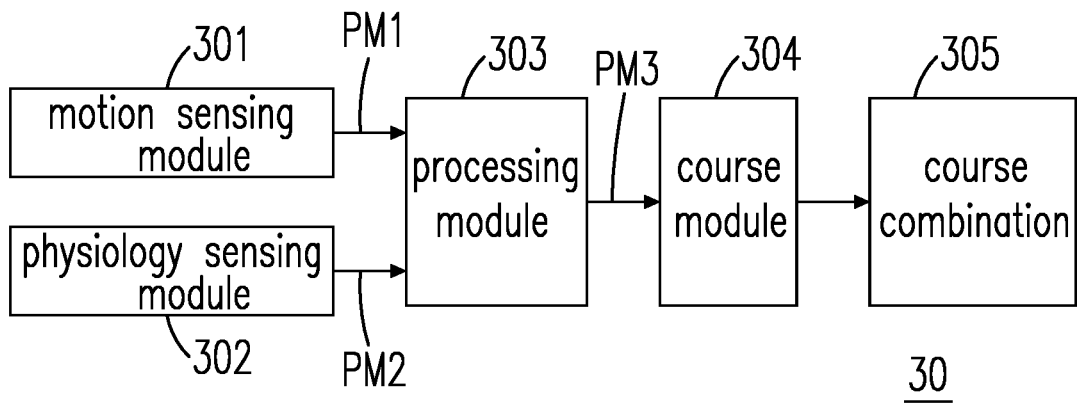

Fig. 9

| |
|---|
| generating a plurality of limb motion signals by sensing a plurality of limb motions of a body builder through a sensing module, and sensing a physiological state of the body builder to generate a physiological state signal via the sensing module. — S101 |
| obtaining a workout characteristic index (WCI) by performing a first calculation related to the plurality of limb motion signals, and obtaining a physiological effect index (PEI) by performing a second calculation associated with the physiological state signal. — S102 |
| obtaining a workout effect index (WEI) by performing a third calculation associated with the WCI and the PEI. — S103 |
| evaluating a plurality of categorical factors associated with the WEI to plan the parameters of the fitness course. — S104 |

Fig. 10

METHOD AND SYSTEM OF PLANNING FITNESS COURSE PARAMETERS

CROSS REFERENCE TO RELATED APPLICATION

This application claims the benefit of Taiwan's Patent Application No. 106146085, filed on Dec. 27, 2017, at Taiwan's Intellectual Property Office, the disclosures of which are incorporated herein in their entirety by reference.

TECHNICAL FIELD

Embodiments in the present disclosure are related to a method and a system of planning fitness course parameters, and more particularly to a method and a system of planning fitness course parameters based on sensing parameters obtained by a sensing module.

BACKGROUND

Modern people pay more attention to health, and their concepts and awareness of health are gradually improved. Therefore, a balanced diet and appropriate exercise can not only maintain a healthy body, but also enhance the body's resistance and stay away from the pain and disease.

Due to the maintenance of health and the growing popularity of cognition for keeping beautiful figures, the fitness exercise has become more popular recently and has become a necessary health activity in daily life. The fitness person or the gym user can use the fitness equipment or exercise under the guidance of the coach, or self-purchasing simple fitness equipment at home to engage in self-training or self-fitness exercise without equipment. Although the fitness exercise effect is closely related to the planning and content of the fitness program, the fitness available time is directly related to the fitness effect no matter the user performs fitness in the gym or self-training at home.

However, in modern life, the average person is working hard to balance the equally important family life. Therefore, the available time for self-use is actually quite urgent, and the available time for fitness is of course unrestricted. Therefore, in the gym, in addition to planning the fitness course content for the students to achieve the desired fitness effect, the fitness instructor is an inevitable to focus on how to make the course content allocation planning to achieve the best fitness effect for the fitness students under the available time. On the other hand, for the fitness exercisers who exercise at home, they do not go to the gym fitness practice, that may be a personal preference, but it is more likely to be a decision to save on transportation time, so the fitness time consideration factor that can be utilized is even more important. As to the relatively short fitness time, it will be extremely important for planning the relevant parameters of the fitness course to achieve the expectation of the same or a specific fitness effect when the fitness student engages the same or similar fitness course content.

However, each person's physical fitness status is different. Under normal conditions, the normal person's fitness can meet the standard of curriculum content under normal conditions, but if the fitness person having big weights or being sick must do exercise properly to lose weight, fitness classes that exceed their load will be critical to their lives, and they must be trained in a step-by-step manner to achieve optimal results. Therefore, it is necessary to tailor the fitness course parameters suitable for the individual according to the individual's physiological condition or the intensity of exercise that can be sustained.

SUMMARY OF EXEMPLARY EMBODIMENTS

Therefore, it is expected that these fitness applications can be run not only on the electronic device, but also connected to the back-end database or server, etc. If the electronic device is connected to the database in the server, statistics can be done for different fitness people to generate big data, remote servers or mobile devices/PCs can also generate fitness classes based on the big data stored in remote databases, in order to advise a body builder to follow the tailor-made fitness courses for individuals. The app also generates a course of exercise for the exercise equipment to advise the body builder to exercise properly.

Therefore, it is expected that there is a fitness application that can not only run on the electronic device in a single machine, but can also arrange the sensing module to the fitness person to sense the physiological parameters of the fitness person. For example, the fitness person is provided with an advice or suggestion of the fitness course according to the heart rate, recovery rate or tiredness (fatigue) degree and whether the exercise strength can meet the standard for the fitness person. The sensing module may include a sensing unit that senses the exercise intensity of the exerciser during exercise, such as an accelerometer that senses at least one limb motion of the exerciser, the gyroscope for measuring the angular acceleration of at least one limb motion of the fitness person. The sensing module may further include a heart rate meter that senses the heart rate of the fitness person, a thermometer that senses the temperature of the fitness person, and the like. The sensing module wirelessly transmits the sensed physiological parameters, acceleration, and angular velocity, transmitted to the electronic device for application analysis. The application suggests parameters of the fitness course according to the data, including the number of item groups, the exercise time and the number of exercise times of each item group, the rest time, the total course time, etc. The application can also adjust the parameters of the fitness class according to the proficiency and willingness of the fitness person. Because the exercise time and frequency of each group will also affect the intensity of the exercise, and the rest will affect tiredness of the muscles or the degree of muscle strength recovery of the exerciser, these factors are also very important for the safety of a bodybuilder who wants to lose weight or who need to exercise properly after a sickness or injury, especially for avoiding the exerciser being reluctant to do more exercise than he can to impede health.

In addition, the physiological state of the bodybuilder during exercise and the state of the limb motion can be respectively quantified into a Physiological Effect Index (PEI) and a Workout Characteristic Index (WCI), and a Workout Achievement Index (WAI) can be obtained from the above the two index. Combining with the factors of the proficiency and willingness of the fitness person, it can be quantified into a total Workout Achievement Indicator (WAI). These indexes can be stored in the personal fitness history database, and the application can analyze the personal fitness history data to suggest the parameters of the fitness program for the next workout, so that the total WAI of the fitness person can be optimized.

The object of the present invention is to plan the fitness course content that can obtain the same fitness effect under a short fitness time condition, or to plan the fitness course content that can obtain better fitness performance under the same fitness time. The configuration of these fitness courses is the parameter configuration of the fitness course content.

Another object of the present invention is to obtain the best fitness training results by adjusting the total number of sports items or single sports item of a newly setting or a predetermined fitness course content, total exercise time, total rest time, number of groups, number of exercises in each group, exercise time of each group, interval between groups or rest time under the constraints of available fitness time and space. The so-called sports items here refer to the fitness exercise of freehand exercise or with aids of equipment. If the sports single item refers to freehand sports items, the fitness sports are such as Bobby jump, opening and closing jump, walking, running or pushing forward. Alternatively, if the sports single item refers to use of equipment, the fitness sports are such as rowing, pedaling, bed bouncing, dumbbell or equipment of flying birds, barbell weightlifting or weight lifting squats and so on.

The so-called best fitness training results can be the maximum calories that can be consumed in the same exercise time, or achieve a maximum exercise coordination or exercise consistency with respect to a standard fitness exercise, exercise to a larger muscle strength or muscle endurance, the most muscle growth or muscle hypertrophy and other fitness results.

The invention provides a system for planning parameters of a fitness course, the system comprises a multiple motion-sensing module, a physiological state sensing module and a data processing unit. The multiple motion-sensing module senses a plurality of limb motions of a body builder to generate a plurality of limb motion signals, and the physiological state sensing module senses a physiological state of the body builder to generate a physiological state signal. The data processing unit configured to implement a first algorithm, a second algorithm, a third algorithm and a fourth algorithm; obtain a workout characteristic index (WCI) based on the first algorithm and the plurality of limb motion signals; obtain a physiological effect index (PEI) based on the second algorithm and the physiological state signal; obtain a workout effect index (WEI) based on the third algorithm, the WCI and the PEI; and evaluate a plurality of categorical factors associated with the WEI based on the fourth algorithm, in order to plan the parameters of the fitness course.

The present invention provides a method for planning parameters of a fitness course, comprising the following steps: generating a plurality of limb motion signals by sensing a plurality of limb motions of a body builder through a sensing module, and sensing a physiological state of the body builder to generate a physiological state signal via the sensing module; obtaining a workout characteristic index (WCI) by performing a first calculation related to the plurality of limb motion signals, and obtaining a physiological effect index (PEI) by performing a second calculation associated with the physiological state signal; obtaining a workout effect index (WEI) by performing a third calculation associated with the WCI and the PEI; and evaluating a plurality of categorical factors associated with the WEI to plan the parameters of the fitness course.

The present invention provides a system for planning parameters of a fitness course, and the system comprises a course module, a motion sensing module, a physiological sensing module, a physiological sensing module and a processing module. The course module has at least one exercise item, a plurality of item parameters associated with the at least one exercise item, and a recommended course combination for a body builder to complete an exercise target. The motion sensing module senses at least one limb motion of the body builder to obtain a first plurality of data associated with the at least one limb motion. The physiological sensing module senses at least one physiological state of the body builder to obtain a second plurality of data associated with the at least one physiological state. The processing module, in response to the first plurality of data and the second plurality of data, developing a third plurality of data associated with the plurality of item parameters to define the recommended course combination to help the body builder to complete the exercise target.

The system's consultative suggestion features and platform-based architecture are not only suitable for fitness activities such as gymnasiums with coaches, but also for fitness exercises at home based on the recommendations of this system.

The above embodiments and advantages of the present invention will become more readily apparent to those ordinarily skilled in the art after reviewing the following detailed descriptions and accompanying drawings.

BRIEF DESCRIPTION OF THE DRAWINGS

FIG. 9 is a schematic diagram of a system for planning parameters of a fitness course according to another preferred embodiment of the present invention.

FIG. 10 is a schematic diagram of a method for planning parameters of a fitness course according to a preferred embodiment of the present invention.

DETAILED DESCRIPTION OF THE PREFERRED EMBODIMENTS

Please refer to all figures of the present invention when reading the following detailed description, wherein all figures of the present invention demonstrate different embodiments of the present invention by showing examples, and help the skilled person in the art to understand how to implement the present invention. However, the practical arrangements and the present method provided to implement the present invention is not necessary to completely comply with the descriptions in the specification. The present examples provide sufficient embodiments to demonstrate the spirit of the present invention, each embodiment does not conflict with the others, and new embodiments can be implemented through an arbitrary combination thereof, i.e., the present invention is not restricted to the embodiments disclosed in the present specification.

Figure 1:
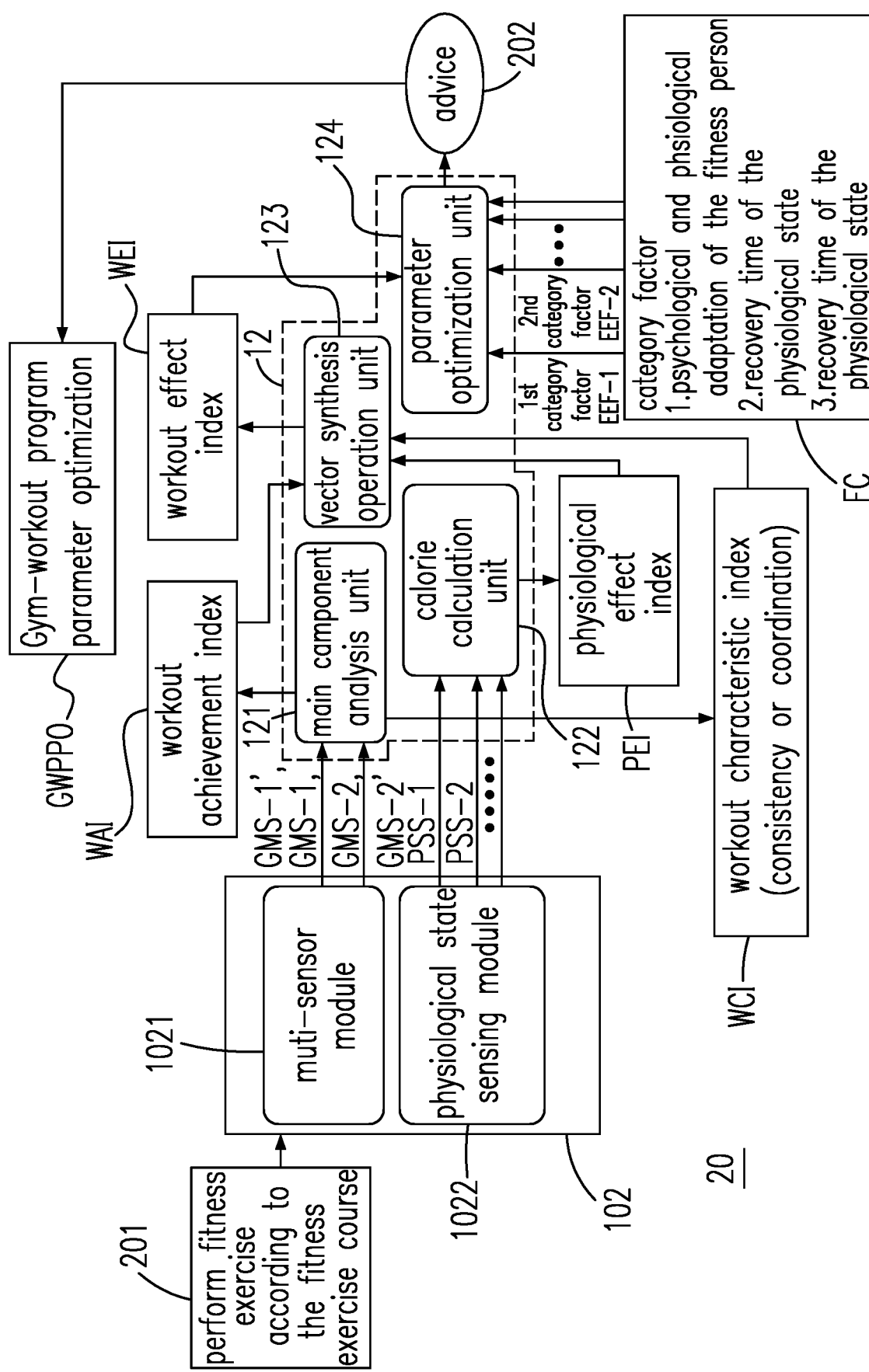
FIG. 1 is a schematic diagram of a system 10 for planning fitness course parameters in accordance with a preferred embodiment of the present invention.

Please refer to FIG. 1, which is a schematic diagram of a system 10 for planning fitness course parameters in accordance with a preferred embodiment of the present invention. Please refer to FIG. 2, which is a schematic diagram of the multiple motion sensing module 1021 being worn on a fitness person in accordance with a preferred embodiment of the present invention.

Figure 2:
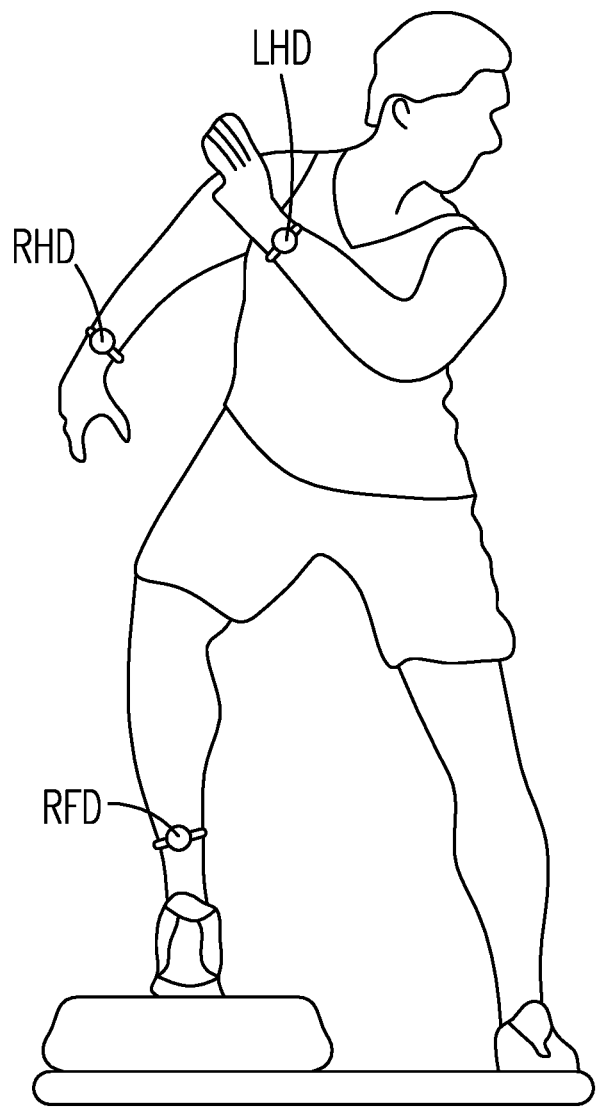
FIG. 2 is a schematic diagram of the multiple motion sensing module 1021 being worn on a fitness person in accordance with a preferred embodiment of the present invention.

The system 10 includes a fitness exercise input device 201 and a display device 202, wherein the fitness exercise input device 201 is used to input a fitness course performed by the fitness person according to contents of a fitness item and at least one fitness item related to the contents. The system 10 further includes a sensing module 102 and a data processing unit 12. The sensing module 102 includes a multiple motion sensing module 1021 and a physiological state sensing module 1022. The multi-motion sensing module 1021 comprises a motion sensor such as an accelerometer, a gyroscope and a geomagnetic instrument. As shown in FIG. 2, the multi-motion sensing module 1021 includes at least one left-hand motion sensing device LHD. a right-hand motion sensing device RHD and a right-foot motion sensing device RFD are worn on a limb of a fitness person. Each of the sensing devices LHD, RHD and RFD includes at least one component such as an accelerometer, a gyroscope and a geomagnetic instrument. When the bodybuilder refers to the fitness schedule for exercise, the sensing devices LHD, RHD, and RFD are used to sense the plurality of limb movements of the fitness person to correspondingly generate a plurality of limb motion sensing signals GMS-1, GMS-2, GMS-1' and GMS-2', etc.

The physiological state sensing module 1022 includes a heart rate meter that can be built in the sensing device LHD, RHD, and RFD, and when the fitness person performing fitness exercises by referring the fitness exercise curriculum, it can be used to sense the physiological state. That is, the heart rate, and a first physiological state signal PSS-1 is correspondingly generated, i.e., a heart rate signal. The physiological state sensing module 1022 can further include a thermometer, which can be built in the sensing devices LHD, RHD, RFD, and when the fitness person performs fitness exercise by referring the fitness exercise curriculum, it is used to sense the temperature, and a second physiological state signal PSS-2 is correspondingly generated, i.e., a temperature signal PSS-2.

The data processing unit 12 has a motion characteristic corresponding function, which utilizes, for example, a principal component signal analysis algorithm (PCA) 121 to perform the plurality of limb motion signals GMS-1, GMS-2, GMS-1', and GMS-2' corresponds to a WCI (Workouts Characteristic Index), such as a motion consistency index or a motion coordination index. The current acceleration signal is represented by GMS-1, and the current angular velocity signal is GMS-2, the personal history or coach's reference acceleration signal is represented by GMS-1', and the personal history or coach's reference angular velocity signal is represented by GMS-2'. The data processing unit 12 further has a physiological state corresponding function, which uses a reference heartbeat to calculate a calorie consumption by a calculation method 122 for mapping the physiological state signal PSS-1 (i.e., the heart rate signal) into a Physiological Effect Index (PEI) representing a calorie consumption; and a fitness effect corresponding function, which uses, for example, a vector synthesis algorithm 123 incorporating the WCI, the WAI (Workouts Achievement Index) and the physiological effect index PEI to converted into a WEI (Workouts Effect Index); and a course parameter revision function, which is based on a parameter optimization algorithm 124, adjusts the content parameters of the training schedule by evaluating a first category factor EEF-1—fitness outcome factors, i.e., the WAI, a second category factor EEF-2—fitness environment factors, such as a time factor, a spatial factor, a distance factor, a third category factor—fitness cost factor, i.e., one cost factors, and a fourth category of factors—fitness and psychological and physiological factors, such as a vitality (health a factor, and a fitness action operation proficiency factor, etc., wherein the content parameters of the training schedule including the exercise sequence of each exercise item or individual item in the exercise course, the entire time of the individual exercise course or operation period configuration or its operation time in each group of the exercise course, the operation period configuration or operation time of the item or single item in the exercise course; or the number of motions, the exercise time, the rest time, the number of repeated cycles, and the like.

For example, when a bodybuilder with a large body weight is exercising, the angular velocity signal and the acceleration signal measured by the multiple motion sensing module 1021 may not reach the standard of the coach, i.e., the standard of the reference angular velocity signal and the reference acceleration signal cannot be met, and when the heart rate or the body temperature sensed by the sensing module 1022 is relatively high compared with the average person, the data processing unit 12 can split the sports item into a plurality of time periods, and the rest time or the number of rest periods between the exercise time periods can be considered to increase, each exercise period can be lengthened, and the number of each exercise period can be reduced. It is in anticipation of achieving the same effect of completing all the motions in a single time period, for example, the total calories burned by the exercise is the same, but it will not endanger the health of the fitness person having the big weight due to exceed the load to which the fitness person can afford.

In FIG. 1, the data processing unit 12 corresponds the plurality of limb motion signals GMS-1, GMS-2 to a workout characteristic index WCI via a first algorithm (Principal Component Analysis—PCA). The WCI is such as a motion consistency or a quantitative value of motion coordination, used to compare with the standard motion reference signal GMS-1', GMS-2' provided by the coach, such as the consistency between the two signals, thereby judging the training result. Alternatively, the history of the exercise signals of the fitness person can be compared with each other, thereby judging the difference between the present and the history signals, the progress of the fitness exercise of the fitness person can be understood. The PCA algorithm here is used to analyze the acceleration signal GMS-1, GMS-1', angular velocity signal GMS-2, GMS-2' and the information converted by the position-related signal, and then the motion characteristics can be analyzed to derive.

In FIG. 1, the data processing unit 12 applies the physiological state signal PSS-1, PSS-2, such as a heart rate signal PSS-1, to a physiological effect or a physiological phenomenon index PEI via a second method (Caloric Formula). The PEI is such as calorie consumption or oxygen consumption. The calorie consumption is calculated as follows: for men, the calorie consumption=[(age×0.2017)+(body weight× 0.09036)+(heart rate value×0.6309)−55.0969]×exercise time/4.184. For women, the calorie consumption= [(age×0.074)−(body weight×0.05741)+(heart rate value×0.4472)−20.4022]×exercise time/4.184. The physiological effect index PEI can be defined as follows: PEI= $((cb_r/cb_u)^2+(VO_{2\,max\_r}/VO_{2\,max\_u})^2)^{1/2}$, wherein $cb_r$ is a reference calorie consumption, $cb_u$ is a calorie consumption of a fitness person, $VO_{2\,max\_r}$ is a reference maximum oxygen intake, and $VO_{2\,max\_u}$ is the maximum oxygen intake of a fitness person.

In FIG. 1, the workout characteristic index (WCI) and the workout achievement index WAI (exercise training results: muscle strength, muscular endurance, and muscle hypertrophy) and the physiological effect index PEI (or physiological phenomenon) is converted into a workout effect index WEI by a third algorithm (vector synthesis operation), i.e., calculating a quantitative value for the consistency or coordination of exercise, and the product of the muscle strength value, the muscular endurance value or the muscle hypertrophy value and the calorie consumption value or the vector sum. The vector synthesis operation here is the calculation result of the square of the workout characteristic index WCI, the workout achievement index WAI and the physiological effect index PEI, and their sum is root to obtain a calculation result. For example, the calculation formula: $WEI=(WCI^2+WAI^2+PEI^2)^{1/2}$. By analyzing the functional relationship between WEI, WCI, WAI and PEI, the peak distribution of the WEI curve or surface can be understand, the peak value can be obtained, and then the WEI optimization value corresponding to the numerical configuration of the relevant sports course parameters can be obtained to achieve the best effectiveness of the exercise.

Figure 3:
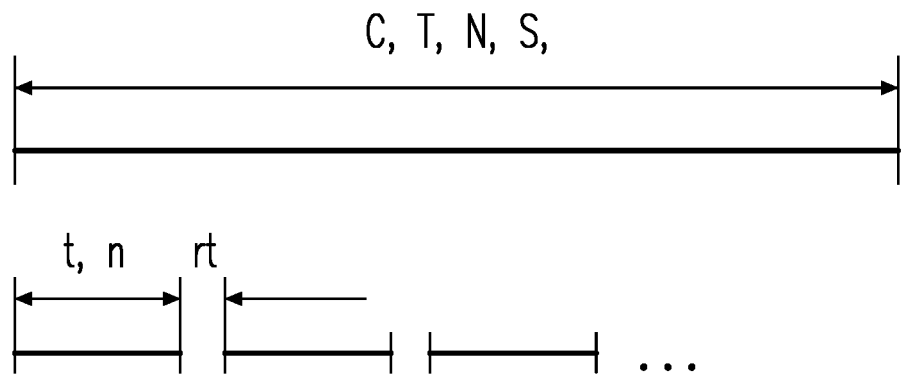
FIG. 3 is a schematic diagram of the fitness course parameters according to the preferred embodiment of the present invention.

Please refer to FIG. 3, which is a schematic diagram of the fitness course parameters of the preferred embodiment of the present invention. The basic parameters of the fitness course include the following:
C: total exercise curriculum time, including total exercise time and total rest time
T: total course time of the curriculum;
N: the total times of motions of a single sport, such as a bobby jump;
S: number of sports groups;
  $S_u$: The number of sports groups in the current fitness exercise;
  $S_r$: Number of sports groups of the standard fitness exercise recorded in the database;
t: exercise time of each group;
n: times of motions per group;
  $n_u$: times of exercises in each group of current fitness exercises;
  $n_r$: times of exercises in each group of standard fitness exercises recorded in the database;
rt: the rest time between the two groups;
  $r_{tu}$: the rest time between two groups of the current fitness exercises;
  $r_{tr}$: the rest time between two groups of the standard fitness exercises recorded in the database;
RT: total rest time of the curriculum.
The relationship between the basic parameters of the above courses is as follows:
$T=Sum(t_i)$, i=1 to S;
$N=Sum(n_i)$, i=1 to S;
$RT=Sum(rt_i)$, i=1 to (S−1);
$C=T+RT$;
The ratio of individual courses to total course parameters is as follows:
TR=rt/T, where TR represents the ratio of rest time between some groups to the total exercise time of the course;
NR=n/N, where NR represents the ratio of the times of motions per group to the total times of motions of a single sport; the greater the TR, the longer the rest time of the bodybuilder to restore tiredness, and the larger the NR, the higher times of motions in each group during the total course time, and the total number of exercise groups is less, that is, the times of breaks between groups is less.

Returning to FIG. 1, the data processing unit 12 analyzes the difference between the plurality of limb motion signals GMS-1, GMS-2 of the bodybuilder and the reference movements of a plurality of limbs of the trainer by using the first algorithm, so as to determine a training result. The system 10 further includes a database (not shown), which may be located at the local end or the server in the network, and stores an instant acceleration value $a_u$/historical acceleration value an, an instant angular velocity value $w_u$/historical angular velocity value $w_h$ and an instantaneous four-element value $q_u$/history four-element value $q_h$ corresponding to the plurality of limb motion signals GMS-1, GMS-2 of the fitness person, and stores a reference acceleration value $a_r$, a reference angular velocity value $w_r$, a reference four-element value $q_r$ corresponding to the reference motion signals GMS1-1', GMS-2' of the plurality of limb motions of the trainer, and stores an acceleration comparison value $a_e$, an angular velocity comparison value $w_e$, and a four-element comparison value $q_e$.

The four elements are used to describe the coordinate representation of the real space. On the basis of the complex, people create a form of four-element q=a+bi+cj+dk to illustrate the vector where the spatial point is located. The four elements can be applied to the description of the limb motions of the exerciser, including the describing of X-axis, Y-axis, and Z-axis rotations of the limb motions, and the calculated quaternion data can be used to compare the differences between the limb motions of the exerciser and the limb motions of the coach, or can be used to compare the progressiveness of the limb motions of the exerciser.

The acceleration comparison value $a_e$ is an error rate between the acceleration value $a_u$ of the fitness person and the reference acceleration value $a_r$, and is equal to $(a_u-a_r)/a_r$; or is an error rate between the acceleration value $a_u$ when the fitness person performs exercise and the history acceleration value $a_h$ of the fitness person, and is equal to $(a_u-a_h)/a_h$. The acceleration value $a_u$ of the workout performed by the fitness person is the sum of the acceleration values of the workout of each group=$Sum(a_{ui})$, i=1 to $S_u$, and the reference acceleration value $a_r$ is the sum of the reference acceleration values of each group.=$Sum(a_{rj})$, j=1 to $S_r$, the historical acceleration value $a_h$ is the sum of the historical acceleration values of each group=$Sum(a_{hk})$, k=1 to $S_h$, and the total acceleration comparison value=$(Sum(a_{ui})-Sum(a_{rj}))/Sum(a_{rj})$, or $(Sum(a_{ui})-Sum(a_{hk}))/Sum(a_{hk})$, i=1 to $S_u$ and j=1 to $S_r$ or k=1 to $S_h$.

The angular velocity comparison value $w_e$ is the error rate between the angular velocity value $w_u$ of the workout performed by the fitness person and the reference angular velocity value $w_r$, and is equal to=$(w_u-w_r)/w_r$; or is the error rate between the angular velocity value $w_u$ of the workout performed by the fitness person and the historical angular velocity value $w_h$, and is equal to=$(w_u-w_h)/w_h$. The instant angular velocity value $w_u$ is the sum of the angular velocity values of the workout of each group, and is equal to Sum($w_{ui}$), i=1 to $S_u$, and the reference angular velocity value $w_r$ is the sum of the reference angular velocity values of each group, and is equal to=Sum ($w_{rj}$), j=1 to $S_r$, the historical angular velocity value $w_h$ is the sum of the historical angular velocity values of each group, and is equal to =Sum($w_{hk}$), k=1 to $S_h$, and the total angular velocity ratio=(Sum($w_{ui}$)−Sum($w_{rj}$))/Sum($w_{rj}$), or (Sum($w_{ui}$)−Sum($w_{hk}$))/Sum($w_{hk}$), i=1 to $S_u$ and j=1 to $S_r$ or k=1 to $S_h$.

The four-element comparison value qe is an error rate between the four-element value qu of the workout performed by the fitness person and the reference four-element value qr, or an error rate between a four-element value qu of the workout performed by the fitness person and the history record four element value qh. The four-element value qu of the workout performed by the fitness person is the sum of the four elements of workout in each group, and is equal to=Sum(qui), i=1 to Su. The reference four-element value qr is the sum of the reference four-element value of each group, and is equal to=Sum(qrj), j=1 to $S_r$. The historical four-element value qh is the sum of the four-element values of the history of each group, and is equal to=Sum(qhk), k=1 to Sh. The total four-element comparison value equal to=(Sum (qui)−Sum(qrj))/Sum(qrj), or (Sum(qui)−Sum(qhk))/Sum (qhk),i=1 to Su and j=1 to Sr or k=1 to Sh.

The workout characteristic index WCI in FIG. 1 is a quantized value that quantizes a motion coordination or consistency of the bodybuilder, and the data processing unit 12 obtains the motion characteristic index WCI by calculating an equation of the motion characteristic index. WCI, the workout characteristic index WCI can be defined as $WCI=(a_e^2+w_e^2+q_e^2)^{1/2}$, $WCI=1-a_e^2+w_e^2+q_e^2)^{1/2}$ or $WCI=1-/(a_e^2+w_e^2+q_2^2)^{1/2}$, etc., or it is an equation formed by other representation methods. As for the equations suitable for estimating the WCI index, they can be used based on the error rates $a_e$, we and $q_e$ defined in different ways. From the calculation formula of the acceleration comparison value $a_e=(a_u-a_r)/a_r$; or $(a_u-a_h)/a_h$, when the acceleration value au of the workout of the fitness person approximates the reference acceleration value $a_r$ of the coach, or when the acceleration value $a_u$ of the workout is approximate to the workout record acceleration value a of the fitness person, the smaller the acceleration comparison value $a_e$ is, the larger the workout characteristic index WCI will be. This represents the fitness coordination of the fitness person is close to the coordination of the coach under the comparison, the fitness action of the fitness person is better consistent with the fitness action of the coach. Alternatively, under the comparison between the current/immediate motion signal and the history records of the fitness person, the workout of the fitness person has less variance of coordination and consistency. Similarly, the angular velocity comparison value $w_e$ and the four-element comparison value $q_e$, are similar to the acceleration comparison value $a_e$.

In another preferred embodiment, if the workout characteristic index WCI=($a_e$2+$w_e$2+$q_e$2) ½, the acceleration comparison value $a_e$ may be another formula, such as $a_e=a_r/(a_u-a_r)$, the angular velocity comparison value can be another formula, such as $w_e=w_r/(w_u-w_r)$, the four-element comparison value $q_e$ can be another formula, such as $q_e=q_r/(q_u-q_r)$. When the acceleration value au of the workout of the fitness person is close to the reference acceleration value $a_r$ of the coach, or the acceleration value $a_u$ of the workout of the fitness person is close to the historical record acceleration value $a_h$ of the fitness person, the greater the acceleration comparison value $a_e$ is, the WCI will also be larger, which means that the coordination the workout of the fitness person is close to the coordination of the coach by the comparison, or the consistency between the fitness motions of the fitness person and the coach matches better. Alternatively, by comparing the history records and the present record of the exerciser, the exerciser's coordination and consistency are less variable. Similarly, the angular velocity comparison value $w_e$ and the four-element comparison value qe are similar to the acceleration comparison value $a_e$. In addition, specific motion characteristic index can be defined, such as the motion acceleration characteristic index $WCI_a=a_e$, the motion angular velocity characteristic index $WCI_w=w_e$ and the motion rotation vector characteristic index $WCI_q=q_e$. By comparing the specific motion characteristic index, the consistency or coordination between the workout of the exerciser and the instructor can be understood, or the workout consistency/motion coordination between the current workout of the exerciser and the previous workout of the exerciser recorded in the database can be understood.

In FIG. 1, the workout achievement index WAI includes three quantitative targets: muscle strength, muscular endurance and muscle hypertrophy; muscle strength refers to the maximum strength exerted against a certain resistance in a muscle contraction; muscular endurance refers to the time or repetition of the muscles that can continue to exert force when using certain muscle strength; muscle hypertrophy refers to the phenomenon that the muscle tissue of the body becomes thicker. Here $w_e$ define the workout achievement index $WAI=1/((ms_u-ms_r/ms_r)^2+(me_u-me_r/me_r)^2+(mh_u-mh_r/mh_r)^2)^{1/2}$, where $ms_u$ is a muscle strength value of the body builder, $ms_r$ is a reference muscle strength value, $me_u$ is a muscle endurance value of the body builder, $me_r$ is a reference muscle endurance value, $mh_u$ is a muscle hypertrophy value of the body builder, and $mh_r$ is a reference muscle hypertrophy value. When the fitness person's muscle strength value $ms_u$ is greater than the reference muscle strength value $ms_r$, the fitness person's muscular endurance value $me_u$ is greater than the reference muscular endurance value $me_r$, and the fitness person's muscle hypertrophy value $mh_u$ is greater than the reference muscle hypertrophy value $mh_r$, the above expression shows that the WAI will also be larger, which means that the exerciser's workout ability is improved, or better than the general standard, and vice versa. In another preferred embodiment, the workout achievement index $WAI=1/((ms_r/ms_u)^2+(me_r/me_u)^2+(mh_r/mh_u)^2)^{1/2}$, the WAI value is opposite to the above example, that is, when the muscle strength value $ms_u$ of the bodybuilder is greater than the reference muscle strength value $ms_r$, the muscular endurance value $me_u$ of the bodybuilder is greater than the reference muscular endurance value $me_r$, and the muscle hypertrophy value $mh_u$ of the body builder is greater than the reference muscle hypertrophy value $mh_r$, the WAI will be smaller. If the workout effect index is defined as follows: WEI=1−(WCI2+WAI2+PEI2)(½), the WEI will become larger as $ms_u$, $ms_r$ and $me_u$ become larger, which can also indicate a better fitness achievements.

In addition to generating the workout effect index WEI according to the workout characteristic index WCI, the workout achievement index WAI and the physiological effect index PEI, other factors may be quantified and added to adjust parameters of the exercise course. For example, the level of fitness, physical factors, and psychological factors of the fitness person can be used as an adjustment factor. For example, the operation proficiency of the fitness items or a single item of the fitness person is associated with the measured acceleration a, a speed V, four elements q, and the setting of course parameters such as S, n, t, rt. Here, a level factor L is defined, the Gym beginner, whose Lb value is between (1.00, 1.30), the Gym Intermediate, whose Lm value is between (1.00, 0.85). and Gym Expert (Gym Advancer), whose La value is between (0.85, 0.70). The values Lb, Lm, and La of the level factor L are related to the number of exercise groups Su. The more advanced fitness class is, the lower the value is. It means that the fitness person can do workout by a smaller number of groups under the same total workout times, and the repetition times of motions in the group is higher, so each group's workout requires stronger muscle strength or muscular endurance. That is, by selecting appropriate values of factors such as Lb, Lm, or La, the value of the workout course parameters suitable for the fitness beginner, the fitness advanced person or the fitness expert can be adjusted correspondingly.

The physiological factors include the recovery rate Rr or the degree of tiredness (or fatigue) Fr, which may be related to the measured acceleration a, angular velocity w and quaternion or orientation vector q. The physiological factors associated with the recovery rate value Rr or the degree of the tiredness (fatigue) value Fr is between (0.10, 1.00), or may not directly set the adjustment factor for physiological factors such as the recovery rate or the degree of tiredness, but let these physiological factors directly relate to the measured physical quantities a, w and q.

Psychological factors include the subjective willing factor Jr of the bodybuilder, which may include the comfort of the fitness environment or the work and rest considerations of the fitness person, etc., thereby affecting the fitness intentions of the fitness person. For example, C, T, N, S, t, n subjective selection of the parameters of the fitness course, and the subjective willing factor value Jr can be between (0.50, 1.50).

After sensing the motion state and the physiological state of the user, the data processing unit 12 can comprehensively calculate the workout effect index WEI, and the system 10 can directly plan the parameters of the fitness exercise course according to the workout effect index WEI, and can continuously take the following factors into consideration, such as the level of fitness, physical factors and psychological factors, in order to adjust the parameters of the fitness items. For example, the user can directly specify the course parameter T, or T and N. Alternatively, the system 10 can refer to the system fitness course database and/or the personal fitness course database of the fitness person to suggest workout course parameters C, N, S, t, n, rt.

In another preferred embodiment, the system 10 or the user can adjust the system's proposed workout course parameters C, N, S, t, n, rt by the level factor L, Lb, Lm and La to form course parameters NL, SL, $t_L$, $n_L$, $rt_L$ of the fitness level recommended for workout.

In another preferred embodiment, the system 10 or the user can adjust exercise course parameters C, N, S, t, n, rt of the system's advice to form the recommended course parameters $C_R$, $N_R$, $S_R$, $t_R$, $n_R$, $rt_R$ or $C_F$, $N_F$, $S_F$, $t_F$, $n_F$, $rt_F$ associated with the physiological recovery rate or the degree of tiredness by the physiological recovery rate value Rr or the degree of tiredness value Fr. Alternatively, adjust the recommended course parameters $C_L$, $N_L$, $S_L$, $t_L$, $n_L$, $rt_L$ for the fitness level by the physiological recovery rate value Rr or the degree of tiredness value Fr, make it be the fitness level course parameters $C_{LR}$, $N_{LR}$, $S_{LR}$, $t_{LR}$, $n_{LR}$, $rt_{LR}$ or $C_{LF}$, $N_{LF}$, $S_{LF}$, $t_{LF}$, $n_{LF}$, $rt_{LF}$ associated with physiological recovery rate or the degree of tiredness.

In another preferred embodiment, the system 10 or the user can adjust the system's recommended workout course parameters C, N, S, t, n, rt by psychological factors, that is, the subjective willing factor of the fitness person, in order to make it be the workout course parameters $C_J$, $N_J$, $S_J$, $t_J$, $n_J$, $rt_J$ recommended by the system 10 according to the subjective willingness of the fitness person. Alternatively, by using the psychological factors, the system 10 can adjust the physiological state recommendation course parameters $C_R$, $N_R$, $S_R$, $t_R$, $n_R$ $rt_R$ or $C_F$, $N_F$, $S_F$, $t_F$, $n_F$, $rt_F$, which are related to the physiological recovery rate or the degree of tiredness, and make it be a physiological state recommendation course parameters $C_{RJ}$, $N_{RJ}$, $S_{RJ}$, $t_{RJ}$, $n_{RJ}$, $rt_{RJ}$ or $C_{FJ}$, $N_{FJ}$, $S_{FJ}$, $t_{FJ}$, $n_{FJ}$, $rt_{FJ}$ according to the subjective willingness of the fitness person. Alternatively, by using the psychological factors, the system 10 can adjust the fitness level recommended course parameters $C_L$, $N_L$, $S_L$, $t_L$, $n_L$, $rt_L$ to make it be a fitness level recommendation course parameters $C_{LJ}$, $N_{LJ}$, $S_{LJ}$, $t_{LJ}$, $n_{LJ}$, $rt_{LJ}$ according to the subjective willingness of the fitness person. Alternatively, by using the psychological factors, the system 10 can adjust the fitness level course parameters $C_{LR}$, $N_{LR}$, $S_{LR}$, $t_{LR}$, $n_{LR}rt_{LR}$ or $C_{LF}$, $N_{LF}$, $S_{LF}$, $t_{LF}$, $n_{LF}$, $rt_{LF}$ associated with the physiological recovery rate or the degree of the tiredness level, make it be fitness level course parameters $CL_{RJ}$, $NL_{RJ}$, $SL_{RJ}$, $tL_{RJ}$, $nL_{RJ}$, $rtL_{RJ}$ or $NL_{FJ}$, $SL_{FJ}$, $tL_{FJ}$, $nL_{FJ}$, $rtL_{FJ}$ associated with the physiological recovery rate or the degree of the tiredness according to a subjective willingness of the fitness person.

Figure 4:
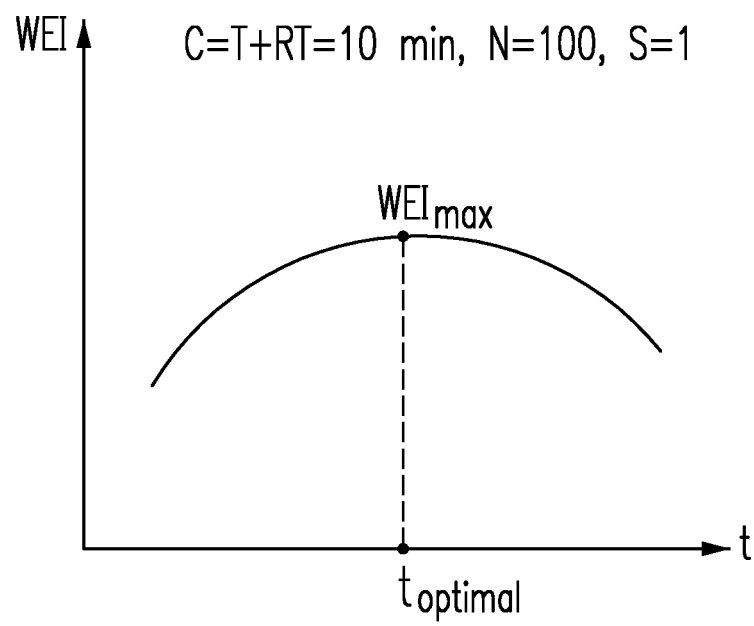
FIG. 4 is a schematic diagram of the relationship between the workout effect index WEI and the workout course parameters according to a preferred embodiment of the present invention.

Please refer to FIG. 4, which is a schematic diagram of the relationship between the workout effect index WEI and the workout course parameters according to a preferred embodiment of the present invention. The horizontal axis represents the exercise time of a single group, and the vertical axis represents the workout effect index WEI. In FIG. 4, taking the workout of Bobby Jump as an example, the total exercise time is C: 10 minutes, the total times of exercises is N: 100 times, and the parameters of the fitness course parameters are configured as follows:

Number of groups S: 1

Bobby Jump, in 10 minutes, completed 100 times in 1 group with no rest.

Course parameter configuration:

Total exercise time: $T<=10$ min, total times of exercises: $N=100$, total exercise course time: $C=T+RT$.

TABLE 1

| S | n | t (min) | rt (min) |
|---|---|---------|----------|
| 1 | 100 | 5 | 5 |
|   |   | 6 | 4 |
|   |   | 7 | 3 |
|   |   | 8 | 2 |
|   |   | 9 | 1 |
|   |   | 10 | 0 |

It can be seen from Table 1 and FIG. 4 that the workout effect index WEI is relatively small when the exercise time t is 5 minutes, the rest time is 5 minutes, and the fitness item is divided into one group. However, as the exercise time t of the group is extended to the range of 7-8 minutes, there is a better workout effect index WEI, which becomes smaller when it reaches 9-10 minutes. This means that under the appropriate fitness course parameters, there will be an optimized workout effect index WEI.

Figure 5:
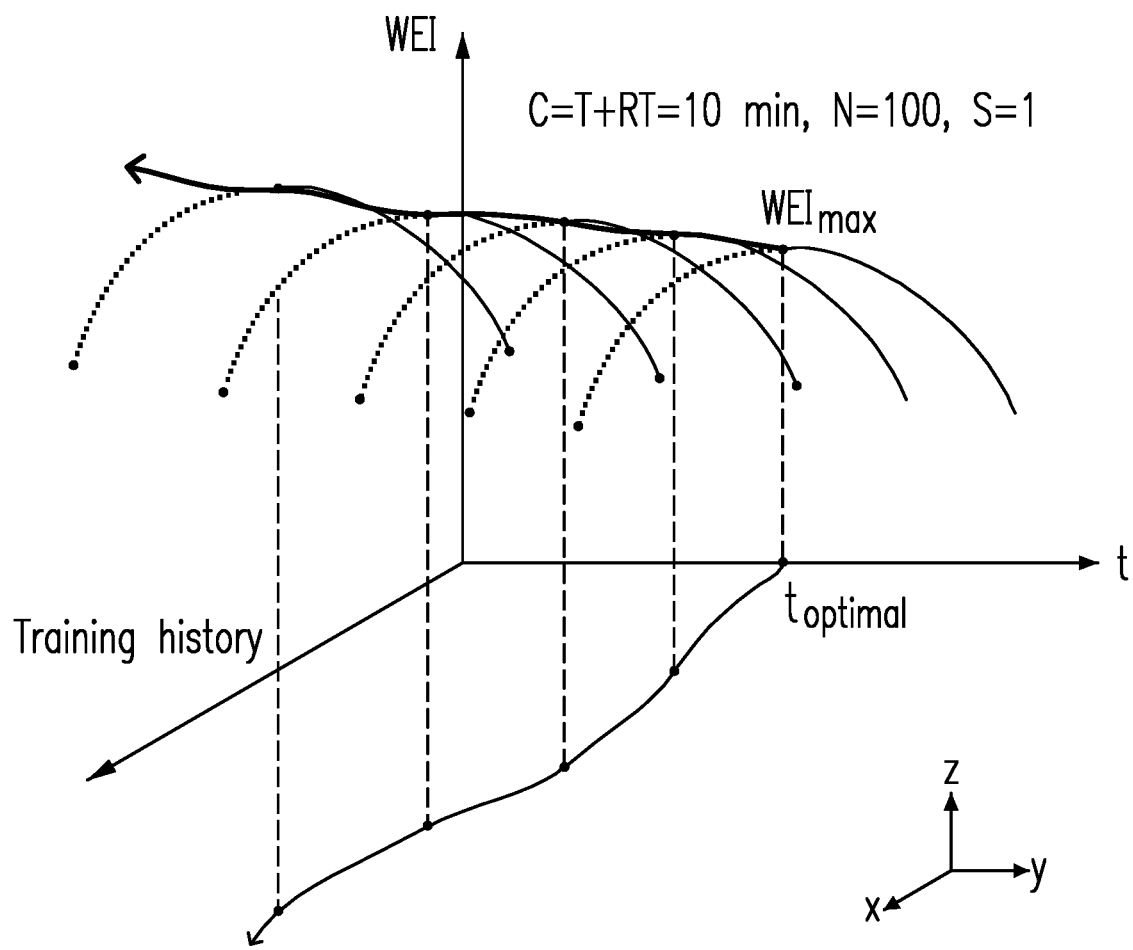
FIG. 5 is a schematic diagram of the workout effect index growing along with the training process according to the preferred embodiment of the present invention.

Please refer to FIG. 5, which is a schematic diagram of the workout effect index growing along with the training process according to the preferred embodiment of the present invention. The y-axis represents the workout time of a single group, the x-axis represents the training course, and the z-axis represents the workout effect index WEI. In FIG. 5, in the case that the workout effect index WEI is only divided into one group, the optimized workout effect index WEI will also be improved along with the training course according to the present invention, and the fitness person can efficiently achieve the effects of optimal muscle strength, muscle endurance, muscle hypertrophy, calorie consumption, and oxygen consumption.

Figure 6:
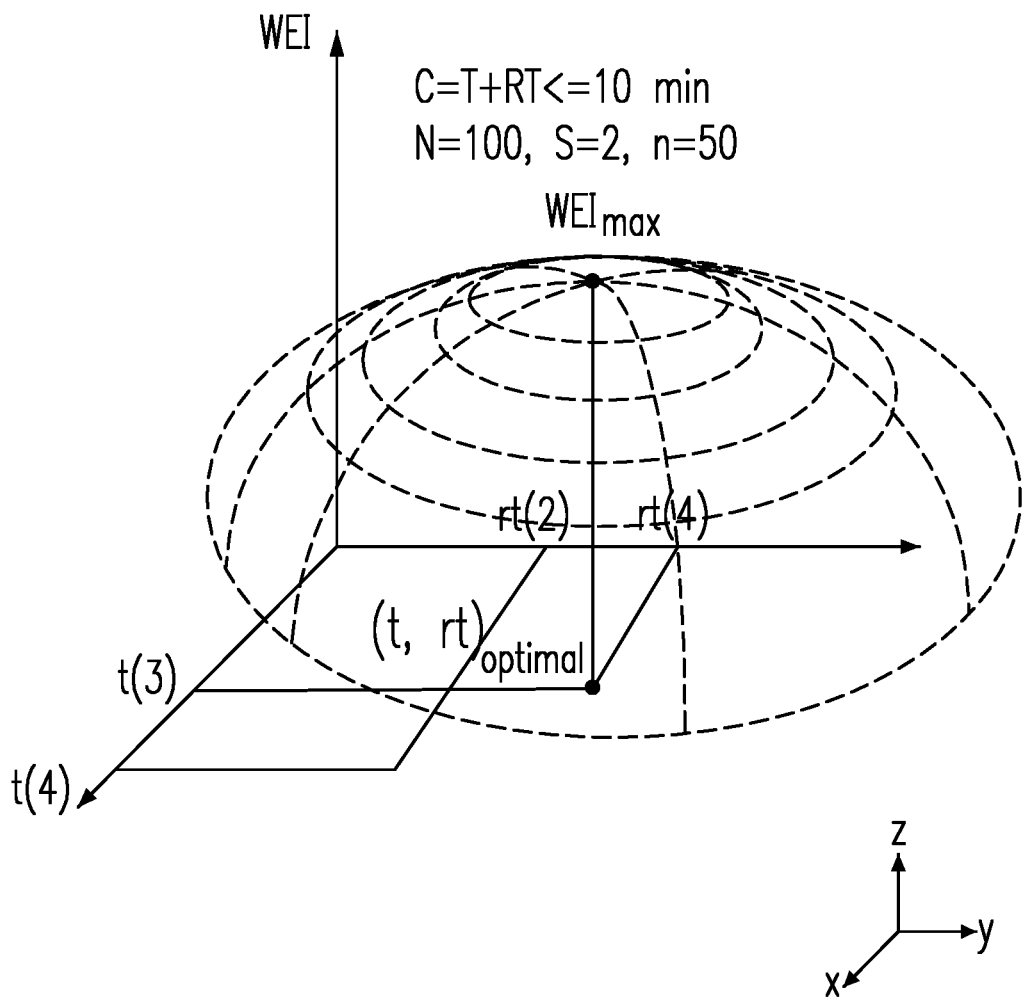
FIG. 6 is a schematic diagram showing the relationship of the exercise time and the rest time associated with the workout effect index WEI according to a preferred embodiment of the present invention.

Please refer to FIG. 6, which is a schematic diagram showing the relationship of the exercise time and the rest time associated with the workout effect index WEI according to a preferred embodiment of the present invention. The y-axis represents the rest time between groups, the x-axis represents exercise time of each group, and the z-axis represents the workout effect index WEI. In FIG. 6, taking the fitness exercise of Bobby Jump as an example, the total exercise time is T<=10 minutes, the total number of exercise times is N:100 times, the number of groups is 2, and the parameters of the fitness course parameters are as follows:

Number of groups S: 2

Bobby jumps, in the total exercise course time C=10 minutes, divided into 2 groups, repeat 50 times in each group, total times is 100 times, there is a rest time between groups.

Course parameter configuration:

Total exercise time: $T<=10$ min, total times of exercises: $N=2\times n=100$, total exercise course time: $C=t\times 2 (=T)+rt=10$.

TABLE 2

| S | n | t (min) | rt (min) |
|---|---|---|---|
| 2 | 50 | 4 | 2 |
| 2 | 50 | 3 | 4 |

It can be seen from Table 2 and FIG. 6 that the total exercise time T of the course is up to 10 minutes. The first course parameter is configured by 50 times in each group, the exercise time is 4 minutes, and the rest time between groups is 2 minutes. The achieved workout effect index WEI is relatively poor. The second course parameter is configured 50 times in each group, the exercise time is 3 minutes, and the rest time between groups is 4 minutes, which can achieve the best workout effect index WEI max.

Figure 7:
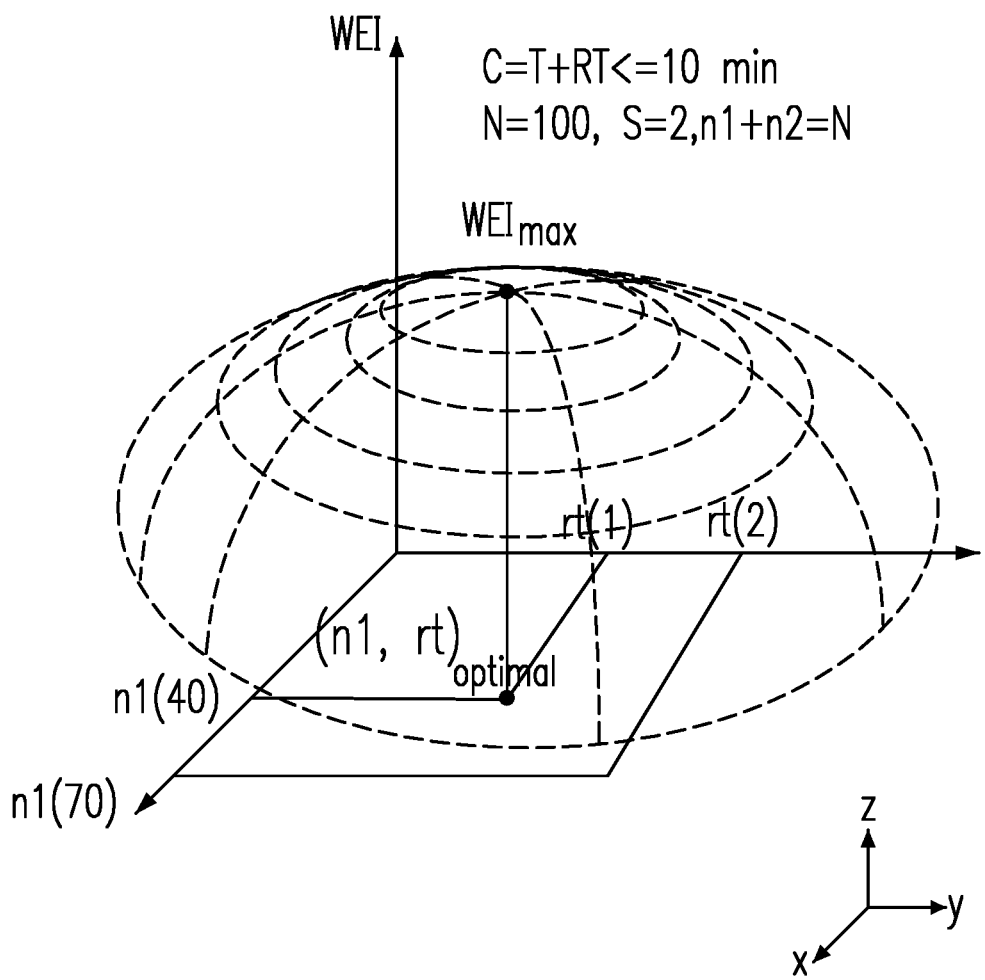
FIG. 7 is a schematic diagram of the relationship of the exercise times and the rest time associated with the workout effect index WEI according to a preferred embodiment of the present invention.

The number of times of each group in a single fitness item may also be different. Please refer to FIG. 7, which is a schematic diagram of the relationship of the exercise times and the rest time associated with the workout effect index WEI according to a preferred embodiment of the present invention. The y-axis represents the rest time between groups. The x-axis represents the times of motions per group, and the z-axis represents the workout effect index WEI. In FIG. 7, taking the fitness exercise of Bobby Jump as an example, the total exercise time is C=10 minutes, the total times of exercises is N: 100, and the number of groups is S=2. The configurations of the fitness course parameters are as follows:

Bobby jumps, in 10 minutes, divided into 2 groups, operation times in each group is different, the total times is 100 times, and the rest time between groups can be different.

Course parameter configuration:

Total exercise time: $T<=10$ min, total times of exercises: $N=n1+n2=100$, total exercise course time: $C=t1+t2(=T)+rt=10$.

TABLE 3

| S | n1 | n2 | t1 (min) | t2 | rt (min) |
|---|---|---|---|---|---|
| 2 | 40 | 60 | 4 | 5 | 1 |
| 2 | 70 | 30 | 2 | 6 | 2 |

It can be seen from Table 3 and FIG. 7. The total exercise course time is 10 minutes. The first course parameters are configured to complete 40 times in 4 minutes in the first group and complete 60 times in 5 minutes in the second group. The rest time between groups is 1 minute, and it can also achieve the best workout effect index WEI. While the second course parameters are configured to complete 70 times in 2 minutes in the first group and complete 30 times in 6 minutes in the second group. The rest time between the groups is 2 minutes, and the workout effect index WEI is relatively poor.

Figure 8:
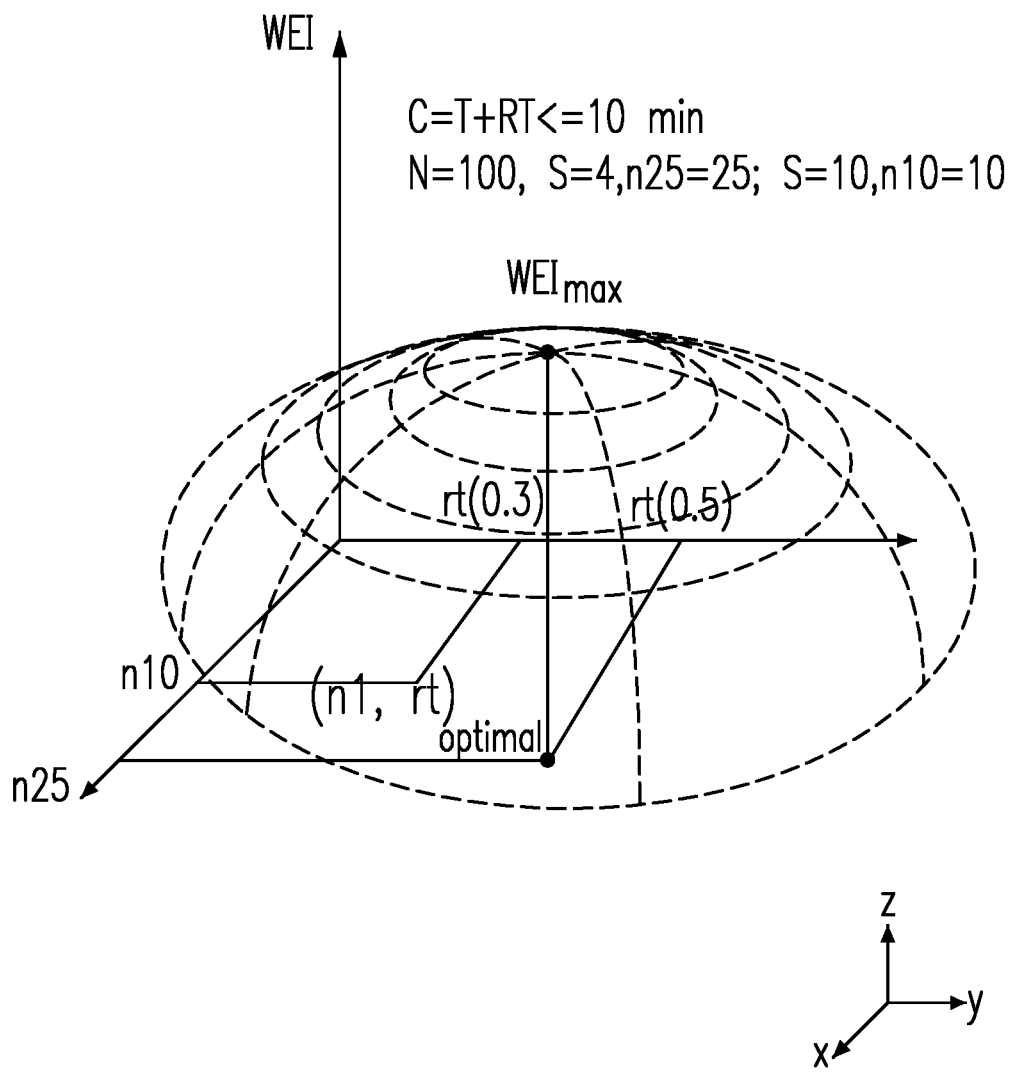
FIG. 8 is a schematic diagram of the relationship of the different rest time, the exercise time and the number of times associated with the workout effect index WEI according to the preferred embodiment of the present invention.

Please refer to FIG. 8, which is a schematic diagram of the relationship of the different rest time, the exercise time and the number of times associated with the workout effect index WEI according to the preferred embodiment of the present invention. The y-axis represents the rest time between groups, and the x-axis represents the times of motions of each group. The z-axis represents the workout effect index WEI. In FIG. 8, taking the Bobby jump as an example. The total exercise time is C=10 minutes, the total times of exercises is N: 100 times, and the number of groups S is greater than 3. The fitness course parameters of the first type are configured as follows:

Bobby jumps, in 10 minutes, divided into 4 groups and performed by 25 times in each group, the total times is 100 times, the operation time in each group or the group break time can be different.

The first course parameter configuration:

Total exercise time: $T<=10$ min, total times of exercises: $N=100$, total exercise course time: $C=4\times t (=T)+3\times rt(=RT)$.

TABLE 4

| S | n | t (min) | rt (min) |
|---|---|---|---|
| 4 | 25 | 2.0 | 0.5 |

The second fitness course parameters in FIG. 8 are configured as follows:

Bobby jump, in 10 minutes, divided into 10 groups, performed by 10 times in each group, the total times is 100 times, the operation time in each group or the group break time can be different.

The second course parameter configuration:

$T<=10$ min, $N=100$, $C=10\times t(=T)+9\times rt(=RT)$.

TABLE 5

| S | n | t (min) | rt (min) |
|---|---|---|---|
| 10 | 10 | 0.7 | 0.3 |

It can be seen from Tables 4 to 5 and FIG. 8 that the second course parameter configuration of the exercise course can achieve an optimized workout effect index WEI max.

Please refer to FIG. 9, which is a schematic diagram of a system 30 for planning parameters of a fitness course according to another preferred embodiment of the present invention. The system 30 includes a course module 304, a motion sensing module 301, a physiological sensing module 302, and a processing module 303. The course module 304 provides a corresponding course combination 305 with at least one exercise item, a plurality of item parameters associated with the at least one exercise item, and a specific fitness exercise completed for an exercise target of the user. The motion sensing module 301 senses at least one limb motion of a fitness person to obtain a first plurality of data PM1 associated to the at least one limb motion. The physiological sensing module 302 senses at least one physiological state of the fitness person to obtain second plurality of data PM2 associated with the at least one limb motions. The processing module 303 respectively assign the third plurality of data PM3 corresponding to the plurality of item parameters according to the first plurality of data PM1 and the second plurality of data PM2, in order to define the corresponding course combination 305, and assist the user to complete the specific fitness exercise.

Please cooperate with FIG. 1, the motion sensing module 301 is a multiple motion sensing module 1021, which senses the plurality of limb motions of the fitness person to generate a plurality of limb motion signals GMS-1, GMS-2, GMS-1', GMS-2'. The physiological sensing module 302 is a physiological state sensing module 1022 that senses the physiological state of the fitness person to generate a physiological state signal PSS-1, PSS-2. The processing module 303 is configured to plan the fitness course parameters based on the plurality of limb motion signals GMS-1, GMS-2, GMS-1', GMS-2' and the physiological state signals PSS-1, PSS-2.

The plurality of item parameters includes at least one of the total exercise course time, the exercise sequence of each exercise course or the individual training sequence, the total exercise time, the individual exercise time or the individual operation time, the configuration time of the exercise item or individual item, the number of the exercise group. the exercise times per group, the exercise time of each group, the rest time between groups, and the total rest time of the exercise course.

The first plurality of data PM1 includes an acceleration comparison value $a_e$, an angular velocity comparison value $w_e$ and a four-element comparison value qe corresponding to the plurality of limb motion signals GMS-1, GMS-2, GMS-1', GMS-2' of the fitness person, the processing module 303 performs a first calculation based on the acceleration comparison value ae, the angular velocity comparison value we and the four-element comparison value qe to obtain the workout characteristic index WCI. The WCI can be defined=$1-(a_e^2+w_e^2+q_e^2)^{1/2}$, and the WCI can be used to quantify the quantized value of the motion coordination or consistency of the bodybuilder.

The second complex data PM2 includes a reference calorie consumption $cb_r$ corresponding to the physiological state signal PSS-1, PSS-2, a fitness calorie consumption $cb_u$ corresponding to the physiological state signal PSS-1, PSS-2, a reference maximum oxygen uptake $VO_{2max\_r}$ corresponding to the physiological state signal PSS-1, PSS-2, and a fitness person maximum oxygen uptake $VO_{2max\_u}$ corresponding to the physiological state signals PSS-1, PSS-2, and the processing module 303 obtains the physiological effect index PEI by calculating an equation of the physiological effect index PEI=$((cb_r/cb_u)^2+(VO_{2max\_r}/VO_{2max\_u})^2)^{1/2}$.

The third plurality data PM3 includes at least one of all period of time C of the individual exercise course, the total exercise time T, the number of exercise groups S, the exercise time t in each group, the rest time rt between groups and the total rest time rt of the exercise session.

The processing module 303 evaluates a fitness exercise performance index WEI=$(WCI2+WAI2+PEI2)$ ½ according to the workout characteristic index WCI, the workout achievement index WAI, and the physiological effect index PEI. The processing module 303 further adjusts the third plurality of data according to a fitness level, a physiological factor, and a psychological factor to optimize the workout effect index WEI, wherein the fitness level includes a beginner level, an advanced level and an expert level, or fitness proficiency related to the workout item of the fitness person. In addition, the physiological factor of the fitness person includes a recovery rate or a degree of fatigue, the psychological factor includes the subjective will of the fitness person. The course combination 305 is like FIGS. 4-8, including configure the total exercise course time C of the single exercise course, the total exercise time T, the number of exercise groups S, the total exercise times N of the single exercise, the exercise times per group. n, exercise time t of each group, break time rt between groups, and total rest time RT of the exercise course, etc., to form a course combination. The fitness item can be a freehand exercise item, such as a push-up, a sit-up, cross-squatting, bobby jumping, etc. Alternatively, the fitness item can be a fitness exercise by using fitness equipment, such as barbell exercise, overhead press, deadlift or front squat.

Please refer to FIG. 10, which is a schematic diagram of a method for planning parameters of a fitness course according to a preferred embodiment of the present invention. Step S101 includes generating a plurality of limb motion signals by sensing a plurality of limb motions of a body builder through a sensing module, and sensing a physiological state of the body builder to generate a physiological state signal via the sensing module. Step S102 includes obtaining a workout characteristic index (WCI) by performing a first calculation related to the plurality of limb motion signals, and obtaining a physiological effect index (PEI) by performing a second calculation associated with the physiological state signal. Step S103 includes obtaining a workout effect index (WEI) by performing a third calculation associated with the WCI and the PEI. Step S104 includes evaluating a plurality of categorical factors associated with the WEI to plan the parameters of the fitness course.

EMBODIMENTS

1. A system for planning parameters of a fitness course comprises a multiple motion-sensing module, a physiological state sensing module and a data processing unit. The multiple motion-sensing module senses a plurality of limb motions of a body builder to generate a plurality of limb motion signals, and the physiological state sensing module senses a physiological state of the body builder to generate a physiological state signal. The data processing unit configured to implement a first algorithm, a second algorithm, a third algorithm and a fourth algorithm; obtain a workout characteristic index (WCI) based on the first algorithm and the plurality of limb motion signals; obtain a physiological effect index (PEI) based on the second algorithm and the physiological state signal; obtain a workout effect index (WEI) based on the third algorithm, the WCI and the PEI; and evaluate a plurality of categorical factors associated with the WEI based on the fourth algorithm, in order to plan the parameters of the fitness course.

2. The system in Embodiment 1, wherein the multiple motion sensing module includes an accelerometer sensing accelerations of the plurality of limb motions of the body builder and a gyroscope sensing an angular velocity of the body builder.

3. The system of any one of Embodiments 1-2, wherein the first algorithm performs a principal component analysis (PCA) method, and the data processing unit analyzes a difference between the plurality of limb motion signals of the body builder and a plurality of reference motion signals of the plurality of limbs of a trainer by using the first algorithm to determine a training result.

4. The system of any one of Embodiments 1-3, further comprising a database for storing an instantaneous/historical acceleration value, an instantaneous/historical angular velocity value and an instantaneous/historical four-element value corresponding to the plurality of limb motion signals of the body builder, storing a reference acceleration value, a reference angular velocity value and a reference four-element value corresponding to the reference motion signals of the plurality of limbs of a trainer, and storing an acceleration comparison value $a_e$, an angular velocity comparison value $w_e$ and a four-element comparison value $q_e$, wherein: the acceleration comparison value $a_e$ is one of an error rate between the instantaneous acceleration value and the reference acceleration value and an error rate between the instantaneous acceleration value and the historical acceleration value; the angular velocity comparison value $w_e$ is one of an error rate between the instantaneous angular velocity value and the reference angular velocity value and an error rate between the instantaneous angular velocity value and the historical angular velocity value; the four-element comparison value $q_e$ is one of an error rate between the instantaneous four-element value and the reference four-element value and an error rate between the instantaneous four-element value and the historical four-element value; the WCI is a value quantifying at least one of a motion coordination and a consistency of the body builder; and the data processing unit obtains the WCI by calculating an equation $WCI=1-(a_e^2+w_e^2+q_e^2)^{1/2}$.

5. The system of any one of Embodiments 1-4, wherein the physiological state sensing module includes a heart rate meter and a thermometer for sensing a physiological state of the body builder; the PEI includes at least one of a calorie consumption and an oxygen consumption amount; the data processing unit estimates the calorie consumption and the oxygen consumption amount of the body builder based on the second algorithm and the physiological state signal, wherein the physiological state signal includes a heart rate signal corresponding to a heart rate value; for men, the calorie consumption amount=[(age*0.2017)+(body weight*0.09036)+(heart rate value*0.6309)−55.0969]*exercise time/4.184; for women, the calorie consumption amount=[(age*0.074)−(body weight*0.05741)+(heart rate value*0.4472)−20.4022]*exercise time/4.184; and the $PEI=((cb_u/cb_r)^2+(VO_{2\ max\_u}/VO_{2\ max\_r})^2)^{1/2}$, wherein $cb_r$ is a reference calorie consumption amount, $cb_u$ is a calorie consumption amount of the body builder, $VO_{2\ max\_r}$ is a reference maximum oxygen intake, and $VO_{2\ max\_u}$ is a maximum oxygen intake of the body builder.

6. The system of any one of Embodiments 1-5, wherein the WEI is one of a product and a vector sum of a motion coordination quantified value and a calorie consumption value; the plurality of categorical factors include at least one of a fitness outcome factor, a time factor, a spatial factor, a fitness environment factor, a health factor, a fitness action operating proficiency factor, a psychological factor of the body builder, a physiological factor, and a preference factor; and the parameters of the fitness course include at least one of a training sequence among exercise items and a single exercise item, a total time of the fitness course, a total time of an exercise item, an operation time of each of the exercise items, a configuration time of each exercise item, an exercise group number, a number of times of the exercise items in a specific exercise group, a time of each exercise group, a rest time between two consecutive exercise groups, and a total rest time of the fitness course.

7. The system of any one of Embodiments 1-6, further comprising a workout achievement index (WAI), wherein the WAI includes muscle strength, muscular endurance, and muscle hypertrophy, where the $WAI=1/((ms_r/ms_u)^2+(me_r/me_u)^2+(mh_r/mh_u)^2)^{1/2}$, $ms_u$ is a muscle strength value of the body builder, $ms_r$ is a reference muscle strength value, $me_u$ is a muscle endurance value of the body builder, $me_r$ is a reference muscle endurance value, $mh_u$ is a muscle hypertrophy value of the body builder, and $mh_r$ is a reference muscle hypertrophy value; the data processing unit evaluates the WEI according to an equation $WEI=(WCI^2+WAI^2+PEI^2)^{1/2}$; and the data processing unit adjusts the parameters of the fitness course to optimize the WEI.

8. A method for planning parameters of a fitness course, comprising the following steps: generating a plurality of limb motion signals by sensing a plurality of limb motions of a body builder through a sensing module, and sensing a physiological state of the body builder to generate a physiological state signal via the sensing module; obtaining a workout characteristic index (WCI) by performing a first calculation related to the plurality of limb motion signals, and obtaining a physiological effect index (PEI) by performing a second calculation associated with the physiological state signal; obtaining a workout effect index (WEI) by performing a third calculation associated with the WCI and the PEI; and evaluating a plurality of categorical factors associated with the WEI to plan the parameters of the fitness course.

9. The method in Embodiment 8, further comprising the following steps of: storing an acceleration comparison value $a_e$, an angular velocity comparison value $w_e$, and a four-element comparison value $q_e$ corresponding to the plurality of limb motion signals of the body builder; and performing the first calculation to obtain the WCI based on an equation $WCI=(a_e^2+w_e^2+q_e^2)^{1/2}$, wherein the WCI is a value that quantifies at least one of a motion coordination and a consistency of the body builder.

10. The method of any one of Embodiments 8-9, further comprising the following steps of: performing the second calculation based on an equation of $PEI=1/((cb_u-cb_r/cb_r)^2+(VO_{2\ max\_r}-VO_{2\ max\_u}/VO_{2\ max\_r})$, wherein $cb_r$ is a reference calorie consumption amount corresponding to the physiological state signal, $cb_u$ is a calorie consumption amount corresponding to the physiological state signal of the body builder, $VO_{2\ max\_r}$ is a reference maximum oxygen intake corresponding to the physiological state signal, and $VO_{2\ max\_u}$ is a maximum oxygen intake corresponding to the physiological state signal of the body builder; and the $WAI=1/((ms_u-ms_r/ms_r)^2+(me_u-me_r/me_r)^2+(mh_u-mh_r/mh_r)^2)^{1/2}$, wherein $ms_u$ is a muscle strength value of the body builder, $ms_r$ is a reference muscle strength value, $me_u$ is a muscle endurance value of the body builder, $me_r$ is a reference muscle endurance value, $mh_u$ is a muscle hypertrophy value of the body builder, and $mh_r$ is a reference muscle hypertrophy value.

11. The method of any one of Embodiments 8-10, further comprising at least one of the following steps: adjusting the parameters of the fitness course according to a fitness level, wherein the parameters of the fitness course include at least one of a training sequence among exercise items and a single exercise item, a total time of the fitness course, a total time of an exercise item, an operation time of each of the exercise items, a configuration time of each the exercise item, an exercise group number, a number of times of the exercise items in a specific exercise group, a training time of each exercise group, a rest time between two consecutive groups, a total rest time of the fitness course, and training proficiency associated with the exercise item, and the fitness level includes beginner level, advanced level and professional level.

12. The method of any one of Embodiments 8-11, further comprising at least one of the following steps: adjusting the parameters of the fitness course according to a physiological factor, wherein the physiological factor includes one of a recovery rate and a degree of tiredness; and adjusting the parameters of the fitness course according to a psychological factor, wherein the psychological factor includes a subjective will of the body builder.

13. A system for planning parameters of a fitness course comprises a course module, a motion sensing module, a physiological sensing module, a physiological sensing module and a processing module. The course module has at least one exercise item, a plurality of item parameters associated with the at least one exercise item, and a recommended course combination for a body builder to complete an exercise target. The motion sensing module senses at least one limb motion of the body builder to obtain a first plurality of data associated with the at least one limb motion. The physiological sensing module senses at least one physiological state of the body builder to obtain a second plurality of data associated with the at least one physiological state. The processing module, in response to the first plurality of data and the second plurality of data, developing a third plurality of data associated with the plurality of item parameters to define the recommended course combination to help the body builder to complete the exercise target.

14. The system in Embodiment 13, wherein the plurality of item parameters include at least one of a training sequence among exercise items, a total time of an individual exercise item, a training time of each of the exercise items, a configuration time of each the exercise item, an exercise group number, a number of times of the exercise items in a specific exercise group, a time of each exercise group, a rest time between two consecutive groups, and a total rest time of the fitness course.

15. The system of any one Embodiments 13-14, wherein the motion sensing module includes an accelerometer sensing an acceleration of the plurality of limb motions of the body builder and a gyroscope sensing an angular velocity of the body builder; and the physiological state sensing module includes a heart rate meter and a thermometer sensing the physiological state of the body builder.

16. The system of any one of Embodiments 13-15, wherein the motion sensing module senses the plurality of limb motions of the body builder to generate a plurality of limb motion signals; the physiological state sensing module senses the physiological state of the body builder to generate a physiological state signal; and the processing module is configured to plan the parameters of the fitness course according to the plurality of limb motion signals and the physiological state signal.

17. The system of any one of Embodiments 13-16, wherein the first plurality of data include an acceleration comparison value $a_e$, an angular velocity comparison value $w_e$, a fusion acceleration and velocity comparison value awe, and a four-element comparison value qe corresponding to the plurality of limb motion signals of the body builder, the processing module performs a first calculation of a workout characteristic index (WCI) based on an equation $WCI=(a_e^2+w_e^2+aw_e^2+q_e^2)^{1/2}$, and the WCI quantifies at least one of a motion coordination and a motion consistency of the body builder; and the second plurality of data include a reference calorie consumption amount $cb_r$ corresponding to the physiological state signal, a calorie consumption amount $cb_u$ corresponding to the physiological state signal, a reference maximum oxygen intake amount $VO_{2\ max\_r}$ corresponding to the physiological state signal, and a maximum oxygen intake $VO_{2\ max\_u}$ corresponding to the physiological state signal, and the processing module calculates a physiological effect index (PEI) based on an equation of $PEI=((cb_u/cb_r)^2+(VO_{2\ max\_u}/VO_{2\ max\_r})^2)^{1/2}$ to obtain the PEI.

18. The system of any one of Embodiments 13-17, further comprising a workout achievement index (WAI), wherein the WAI includes muscle strength, muscular endurance, and muscle hypertrophy, where the $WAI=1/((ms_r/ms_u)^2+(me_r/me_u)^2+(mh_r/mh_u)^2)^{1/2}$, $ms_u$ is a muscle strength value of the body builder, $ms_r$ is a reference muscle strength value, $me_u$ is a muscle endurance value of the body builder, $me_r$ is a reference muscle endurance value, $mh_u$ is a muscle hypertrophy value of the body builder, and $mh_r$ is a reference muscle hypertrophy value.

19. The system of any one of Embodiments 13-18, wherein the third plurality of data include at least one of a total time of an individual exercise course, a number of exercise groups, a number of exercise times per group, an exercise time of each exercise group, a rest time between two consecutive exercise groups, and a total rest time of a full exercise course.

20. The system of any one of Embodiments 13-19, wherein the processing module evaluates a workout effect index (WEI) where $WEI=(WCI^2+WAI^2+PEI^2)^{1/2}$; and the processing module adjusts the parameters of the fitness course according to a fitness level, wherein the parameters of the fitness course include at least one of a training sequence of exercise items and a single exercise item, a total time of the fitness course, a total time of an exercise item, a training time of each of the exercise items, a configuration time of each exercise item, an exercise group number, a number of times of the exercise items in a specific exercise group, a time of each exercise group, a rest time between two consecutive exercise groups, a total rest time of the fitness course, and training proficiency associated with the exercise item, and the fitness level includes beginner level, advanced level and professional level.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A system for planning parameters of a fitness course, comprising:
   a multiple motion-sensing module sensing a plurality of limb motions of a body builder to generate a plurality of limb motion signals;
   a physiological state sensing module sensing a physiological state of the body builder to generate a physiological state signal; and
   a data processing unit configured to:
      implement a first algorithm, a second algorithm, a third algorithm and a fourth algorithm;
      obtain a workout characteristic index (WCI) and a workout achievement index (WAI) based on the first algorithm and the plurality of limb motion signals, wherein the WAI is associated with a muscle of the body builder;
      obtain a physiological effect index (PEI) based on the second algorithm and the physiological state signal, and associated with the physiological state signal;
      obtain a workout effect index (WEI) based on the third algorithm, of calculating a product or a vector sum of the WCI, the WAI and the PEI; and
      impose a fatigue degree as a constraint on the WEI based on the fourth algorithm, in order to plan the parameters of the fitness course and achieve an optimized WEI according to the WCI, the WAI and the PEI.

2. The system as claimed in claim 1, wherein:
   the multiple motion sensing module includes an accelerometer sensing accelerations of the plurality of limb motions of the body builder and a gyroscope sensing an angular velocity of the body builder.

3. The system as claimed in claim 1, wherein:
   the first algorithm performs a principal component analysis (PCA) method, and the data processing unit analyzes a difference between the plurality of limb motion signals of the body builder and a plurality of reference motion signals of the plurality of limbs of trainer by using the first algorithm to determine a training result.

4. The system as claimed in claim 1, further comprising:
   a database for storing an instantaneous/historical acceleration value, an instantaneous/historical angular velocity value and an instantaneous/historical four-element value corresponding to the plurality of limb motion signals of the body builder, storing a reference acceleration value, a reference angular velocity value and a reference four-element value corresponding to the reference motion signals of the plurality of limbs of a trainer, and storing an acceleration comparison value ae, an angular velocity comparison value we and a four-element comparison value $q_e$, wherein:
   the acceleration comparison value ae is one of an error rate between the instantaneous acceleration value and the reference acceleration value and an error rate between the instantaneous acceleration value and the historical acceleration value;
   the angular velocity comparison value we is one of an error rate between the instantaneous angular velocity value and the reference angular velocity value and an error rate between the instantaneous angular velocity value and the historical angular velocity value;
   the four-element comparison value $q_e$ is one of an error rate between the instantaneous four-element value and the reference four-element value and an error rate between the instantaneous four-element value and the historical four-element value;
   the WCI is a value quantifying at least one of a motion coordination and a consistency of the body builder; and
   the data processing unit obtains the WCI by calculating an equation $$WCI = 1 - (a_e^2 + w_e^2 + q_e^2)^{1/2}.$$

5. The system as claimed in claim 1, wherein:
   the physiological state sensing module includes a heart rate meter and a thermometer for sensing a physiological state of the body builder;
   the PEI includes at least one of a calorie consumption and an oxygen consumption amount;
   the data processing unit estimates the calorie consumption and the oxygen consumption amount of the body builder based on the second algorithm and the physiological state signal, wherein the physiological state signal includes a heart rate signal corresponding to a heart rate value;
   for men, the calorie consumption amount=[(age*0.2017)+(body weight*0.09036)+(heart rate value*0.6309)−55.0969]*exercise time/4.184;
   for women, the calorie consumption amount=[(age*0.074)−(body weight*0.05741)+(heart rate value*0.4472)−20.4022]*exercise time/4.184; and
   the PEI=$((cb_u/cb_r)^2+(VO2_{max\_u}/VO2_{max\_r})^2)^{1/2}$, wherein $cb_r$ is a reference calorie consumption amount, cbu is a calorie consumption amount of the body builder, VO2 max_r is a reference maximum oxygen intake, and VO2 max_u is a maximum oxygen intake of the body builder.

6. The system as claimed in claim 1, wherein:
   the WEI is one of a product and a vector sum of a motion coordination quantified value and a calorie consumption value;
   the plurality of categorical factors include at least one of a fitness outcome factor, a time factor, a spatial factor, a fitness environment factor, a health factor, a fitness action operating proficiency factor, a psychological factor of the body builder, a physiological factor, and a preference factor; and
   the parameters of the fitness course include at least one of a training sequence among exercise items and a single exercise item, a total time of the fitness course, a total time of an exercise item, an operation time of each of the exercise items, a configuration time of each exercise item, an exercise group number, a number of times of the exercise items in a specific exercise group, a time of each exercise group, a rest time between two consecutive exercise groups, and a total rest time of the fitness course.

7. The system as claimed in claim 1, wherein:
   the WAI includes muscle strength, muscular endurance, and muscle hypertrophy, where the WAI=$1/((ms_r/ms_u)^2+(me_r/me_u)^2+(mh_r/mh_u)^2)^{1/2}$, $ms_u$ is a muscle strength value of the body builder, $ms_r$ is a reference muscle strength value, $me_u$ is a muscle endurance value of the body builder, mer is a reference muscle endurance value, $mh_u$ is a muscle hypertrophy value of the body builder, and $mh_r$ is a reference muscle hypertrophy value; and
   the data processing unit adjusts the parameters of the fitness course to optimize the WEI.

8. A method for planning parameters of a fitness course, comprising the following steps:
   generating a plurality of limb motion signals by sensing a plurality of limb motions of a body builder through a sensing module, and sensing a physiological state of the body builder to generate a physiological state signal via the sensing module;

obtaining a workout characteristic index (WCI) by performing a first calculation related to the plurality of limb motion signals, and obtaining a physiological effect index (PEI) by performing a second calculation associated with the physiological state signal;

obtaining a workout effect index (WEI) by performing a third calculation, calculating a product or a vector sum and being associated with the WCI and the PEI; and imposing one of a plurality of categorical factors as a constraint on the WEI to plan the parameters of the fitness course and achieve an optimized WEI.

9. The method as claimed in claim 8, further comprising the following steps of:

storing an acceleration comparison value ae, an angular velocity comparison value we, and a four-element comparison value qe corresponding to the plurality of limb motion signals of the body builder; and performing the first calculation to obtain the WCI based on an equation $WCI=(a_e^2+w_e^2+q_e^2)^{1/2}$, wherein the WCI is a value that quantifies at least one of a motion coordination and a consistency of the body builder.

10. The method as claimed in claim 9, further comprising the following steps of:

performing the second calculation based on an equation of $PEI=1/((cb_u-cb_r/cb_r)^2+(VO2_{max\_r}-VO2_{max\_u}/VO2_{max\_r})^{1/2}$, wherein cbr is a reference calorie consumption amount corresponding to the physiological state signal, cbu is a calorie consumption amount corresponding to the physiological state signal of the body builder, VO2 max_r is a reference maximum oxygen intake corresponding to the physiological state signal, and VO2 max_u is a maximum oxygen intake corresponding to the physiological state signal of the body builder; and obtaining a workout achievement index (WAI), wherein the $WAI=1/((ms_u-ms_r/ms_r)^2+(me_u-me_r/me_r)^2+(mh_u-mh_r/mh_r)^2)^{1/2}$, msu is a muscle strength value of the body builder, msr is a reference muscle strength value, $me_u$ is a muscle endurance value of the body builder, $me_r$ is a reference muscle endurance value, $mh_u$ is a muscle hypertrophy value of the body builder, and $mh_r$ is a reference muscle hypertrophy value.

11. The method as claimed in claim 8, further comprising at least one of the following steps:

adjusting the parameters of the fitness course according to a fitness level, wherein the parameters of the fitness course include at least one of a training sequence among exercise items and a single exercise item, a total time of the fitness course, a total time of an exercise item, an operation time of each of the exercise items, a configuration time of each the exercise item, an exercise group number, a number of times of the exercise items in a specific exercise group, a training time of each exercise group, a rest time between two consecutive groups, a total rest time of the fitness course, and training proficiency associated with the exercise item, and the fitness level includes beginner level, advanced level and professional level.

12. The method as claimed in claim 8, further comprising at least one of the following steps:

adjusting the parameters of the fitness course according to a physiological factor, wherein the physiological factor includes one of a recovery rate and a degree of tiredness; and adjusting the parameters of the fitness course according to a psychological factor, wherein the psychological factor includes a subjective will of the bodybuilder.

13. A system for planning parameters of a fitness course, comprising:

a course module having at least one exercise item, a plurality of item parameters associated with the at least one exercise item, and a recommended course combination for a body builder to complete an exercise target;

a motion sensing module sensing at least one limb motion of the body builder to obtain a first plurality of data associated with the at least one limb motion;

a physiological sensing module sensing at least one physiological state of the body builder to obtain a second plurality of data associated with the at least one physiological state;

a processing module, in response to the first plurality of data, and the second plurality of data to obtain a workout characteristic index (WCI), a workout achievement index (WAI) and a physiological effect index (PEI) developing a vector space of a workout effect index (WEI) associated with the WCI, WAI and PEI and by imposing a constraint of a subjective willingness of the body builder to develop a third plurality of data associated with the plurality of item parameters to define the recommended course combination to help the body builder to complete the exercise target.

14. The system as claimed in claim 13, wherein:

the plurality of item parameters include at least one of a training sequence among exercise items, a total time of an individual exercise item, a training time of each of the exercise items, a configuration time of each the exercise item, an exercise group number, a number of times of the exercise items in a specific exercise group, a time of each exercise group, a rest time between two consecutive groups, and a total rest time of the fitness course.

15. The system as claimed in claim 13, wherein:

the motion sensing module includes an accelerometer sensing an acceleration of the plurality of limb motions of the body builder and a gyroscope sensing an angular velocity of the body builder; and the physiological state sensing module includes a heart rate meter and a thermometer sensing the physiological state of the body builder.

16. The system as claimed in claim 13, wherein:

the motion sensing module senses the plurality of limb motions of the body builder to generate a plurality of limb motion signals;

the physiological state sensing module senses the physiological state of the body builder to generate a physiological state signal; and the processing module is configured to plan the parameters of the fitness course according to the plurality of limb motion signals and the physiological state signal.

17. The system as claimed in claim 16, wherein:

the first plurality of data include an acceleration comparison value ae, an angular velocity comparison value we, a fusion acceleration and velocity comparison value awe, and a four-element comparison value qe corresponding to the plurality of limb motion signals of the body builder, the processing module performs a first calculation of the workout characteristic index (WCI) based on an equation $WCI=(a_e^2+w_e^2+aw_e^2+q_e^2)^{1/2}$, and the WCI quantifies at least one of a motion coordination and a motion consistency of the body builder; and the second plurality of data include a reference calorie consumption amount $cb_r$ corresponding to the physiological state signal, a calorie consumption amount $cb_u$ corresponding to the physiological state signal, a reference maximum oxygen intake amount VO2 max_r corresponding to the physiological state signal, and a maximum oxygen intake VO2 max_u corresponding to the physiological state signal, and the processing module calculates the physiological effect index (PEI) based on an equation of $PEI=((cb_u/cb_r)^2+(VO2_{max\_u}/VO2_{max\_r})^2)^{1/2}$ to obtain the PEI.

18. The system as claimed in claim 13, further comprising the workout achievement index (WAI), wherein:
the WAI includes muscle strength, muscular endurance, and muscle hypertrophy, where the $WAI=1/((ms_r/ms_u)^2+(me_r/me_u)^2+(mh_r/mh_u)^2)^{1/2}$, msu is a muscle strength value of the body builder, $ms_r$ is a reference muscle strength value, $me_u$ is a muscle endurance value of the body builder, $me_r$ is a reference muscle endurance value, $mh_u$ is a muscle hypertrophy value of the body builder, and $mh_r$ is a reference muscle hypertrophy value.

19. The system as claimed in claim 13, wherein:
the third plurality of data include at least one of a total time of an individual exercise course, a number of exercise groups, a number of exercise times per group, an exercise time of each exercise group, a rest time between two consecutive exercise groups, and a total rest time of a full exercise course.

20. The system as claimed in any one of claim 17, further comprising the workout achievement index (WAI), wherein:
the processing module evaluates the workout effect index (WEI) where $WEI=(WCI^2+WAI^2+PEI^2)^{1/2}$; and
the processing module adjusts the parameters of the fitness course according to a fitness level, wherein the parameters of the fitness course include at least one of a training sequence of exercise items and a single exercise item, a total time of the fitness course, a total time of an exercise item, a training time of each of the exercise items, a configuration time of each exercise item, an exercise group number, a number of times of the exercise items in a specific exercise group, a time of each exercise group, a rest time between two consecutive exercise groups, a total rest time of the fitness course, and training proficiency associated with the exercise item, and the fitness level includes beginner level, advanced level and professional level.

* * * * *